United States Patent [19]
Olivier et al.

[11] Patent Number: 5,892,124
[45] Date of Patent: Apr. 6, 1999

[54] PROCESS FOR DIENOIC CONDENSATION KNOWN AS THE DIELS-ALDER REACTION

[75] Inventors: Hélène Olivier, Rueil-Malmaison; André Hirschauer, Montesson, both of France

[73] Assignee: Institut Français du Pétrole, France

[21] Appl. No.: 999,390

[22] Filed: Dec. 29, 1997

[30] Foreign Application Priority Data

Dec. 27, 1996 [FR] France ................................. 96 16092

[51] Int. Cl.⁶ .................................................. C07C 49/623

[52] U.S. Cl. ............................................ 568/374; 568/377

[58] Field of Search ..................... 568/377, 374

[56] References Cited

FOREIGN PATENT DOCUMENTS 2 728 180  6/1996  France .

OTHER PUBLICATIONS

Kagan & Riant, "Catalytic Asymmetric Diels–Alder Reactions", *Chem. Rev.,* 92:1007–1019, 1992.
Otto et al., "Lewis Acid Catalysis of a Diels–Alder Reaction in Water", *J. Am. Chem. Soc.,* 118:7702–7702, 1996.

*Primary Examiner*—Floyd D. Higel
*Attorney, Agent, or Firm*—Millen, White, Zelano, & Branigan, P.C.

[57] ABSTRACT

Improved process for implementing the Diels-Alder reaction that consists in using reagents in the presence of at least one liquid salt of general formula $Q^+A^-$, in which $Q^+$ represents a quaternary ammonium and/or phosphonium and $A^-$ represents an anion and optionally at least one Lewis acid. The anion is preferably selected from the group that is formed by tetrafluoroborate, hexafluorophosphate, hexafluoroantimonate, hexafluoroarsenate, perfluoroalkylsulfonate, fluorosulfonate or else dichlorocuprate, tetrachloroborate, tetrachloroaluminate, and trichlorozincate. At the end of the reaction, the organic phase is separated, and the polar phase is reused.

26 Claims, No Drawings

PROCESS FOR DIENOIC CONDENSATION KNOWN AS THE DIELS-ALDER REACTION

FIELD OF THE INVENTION

The object of this invention is an improved process for carrying out the so-called Diels-Alder reaction.

BACKGROUND OF THE INVENTION

The dienoic condensation or cycloaddition [4π+2π], which is also known as the Diels-Alder reaction, is the most important method for synthesizing hexacyclic structures. It consists in thermally reacting a diene that is conjugated on a dienophile, which can be the diene itself, another diene or a monoene, resulting in a 1:1 adduct. When the reactivity of the diene or the dienophile is low, it is necessary to operate at high temperature; this often leads to undesirable polymerization reactions of the diene or polyaddition of the adduit. By contrast, the regioselectivity, diastereofacial selectivity, and the cis/trans ratio of the condensation are fixed and do not always correspond to the product that is sought.

For this reason, it has been proposed that organic solvents be used to improve the speed, regioselectivity, and stereoselectivity of these reactions. In addition to the fact that the effect of these solvents is relatively limited, however, their use poses the problem of separating them from reagents and products.

It has also been proposed to implement the Diels-Alder reaction in the presence of water. The effect of water, or water-rich aqueous alcohol solutions, on the reaction speed is often significant. Furthermore, the endo/exo ratio is always higher there than in the organic medium. The presence in the water of mineral salts, such as lithium salts, further accelerates the reaction.

Furthermore, it has been shown that the Lewis acids, such as $TiCl_4$, $BF_3$ or $AlEtCl_2$, and their alkoxy substitutes, and various cationic complexes of transition metals with acid properties enhance the reaction and its stereoselectivity. In this case, the reaction can be considered as catalyzed. The presence of optically active groups in these compounds also makes it possible to induce a catalytic enantioselective reaction.

All of these effects have been discussed in articles published in Chemical Reviews by U. Pindur and Associates, Vol. 93, p. 741, and by H. Kagan and O. Riant, Vol. 92, p. 1007.

Very recently, J. Engberts and Associates showed in an article in the Journal of the American Chemical Society, Vol. 118, p. 7702, that the combined effect of water and certain weak Lewis acids such as the nitrates of Co, Cu, Ni and Zn made it possible to carry out at ambient temperature Diels-Alder reactions with fairly unreactive dienophiles, and to do so at significant speeds. In contrast, the growing endo/exo ratio observed in pure water disappeared in the presence of a Lewis acid.

SUMMARY OF THE INVENTION

It has now been found, which constitutes the object of this invention, that in the presence of at least one liquid organic-inorganic salt of general formula $Q^+A^-$, in which $Q^+$ represents a quaternary ammonium and/or quaternary phosphonium and $A^-$ represents an anion, the Diels-Alder reactions were significantly accelerated and their stereoselectivity was modified. This offers a certain number of advantages. Since the reagents and the products obtained from the reaction are only sparingly or very sparingly soluble in these media, it is easy to separate them. Furthermore, these media are excellent solvents of a large number of salts and complexes with an ionic nature, in particular the complexes that are sensitive to water, known for catalyzing the reaction. Thus, to the beneficial effect of the ionic medium is added the effect of the catalyst. The easy separation of the medium-catalyst fraction makes it possible to use expensive complexes, in particular complexes that contain asymmetrical inductors. The use of non-aqueous ionic media therefore offers appreciable advantages over organic solvents, which are difficult to separate (as Kagan and Riant have emphasized) or over water, which proteolyses a number of complexes.

More specifically, the invention relates to a process for so-called Diels-Alder dienoic synthesis, characterized in that synthesis is carried out in a medium that is selected from the group that is formed by the media that consist of at least one liquid ammonium salt and/or quaternary phosphonium of general formula $Q^+A^-$, in which $Q^+$ represents a quaternary ammonium and/or phosphonium and $A^-$ represents an anion, and characterized by the media, which comprise at least one liquid salt of quaternary ammonium and/or phosphonium of general formula $Q^+A^-$, in which $Q^+$ represents a quaternary ammonium and/or phosphonium and $A^-$ represents an anion and at least one catalyst, with this catalyst being constituted by a Lewis acid.

The liquid ionic media according to the invention have for a general formula $Q^+A^-$, in which $Q^+$ represents a quaternary ammonium and/or a quaternary phosphonium and $A^-$ represents any anion that is known to be likely, in a non-coordinating way, to form a liquid salt at a low temperature, i.e., below 150° C. and advantageously more than 80° C., and preferably below 50° C., such as preferably the tetrafluoroborate, hexafluorophosphate, hexafluoroantimonate, hexafluoroarsenate ions, the perfluorosulfonates, more specifically the perfluoroalkylsulfonates (for example trifluoromethylsulfonate), and fluorosulfonate. It is also possible, but not preferred, to use the dichlorocuprate, tetrachloroborate, tetrachloroaluminate, trichlorozincate anions. The quaternary ammonium and/or phosphonium preferably correspond to general formulas $NR^1R^2R^3R^4$ and $PR^1R^2R^3R^{4+}$, or to general formulas $R^1R^2N=CR^3R^{4+}$ and $R^1R^2P=CR^3R^{4+}$ where $R^1$, $R^2$, $R^3$ and $R^4$, which are identical or different, represent hydrogen with the exception of cation $NH_4^+$ and preferably a single substituent can represent hydrogen, or hydrocarbyl radicals that have 1 to 12 carbon atoms, for example, saturated or unsaturated alkyl groups, cycloalkyl or aromatic groups, aryl or aralkyl groups that comprise 1 to 12 carbon atoms. The ammonium and/or phosphonium can also be derivatives of nitrogenous or phosphorus heterocycles that comprise 1, 2 or 3 nitrogen and/or phosphorus atoms, with general formulas:

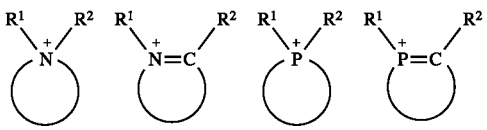

in which the cycles consist of 4 to 10 atoms, preferably 5 to 6 atoms, with $R^1$ and $R^2$ being defined as above. The quaternary ammonium or phosphonium can also be a cation of formula:

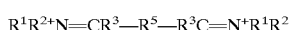

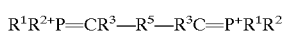

in which $R^1$, $R^2$, $R^3$, which are identical or different, are defined as above, and $R^5$ represents an alkylene or phenylene radical. Among the groups $R^1$, $R^2$, $R^3$ and $R^4$, the radicals methyl, ethyl, propyl, isopropyl, butyl, sec-butyl, tert-butyl, amyl, methylene, ethylidene, phenyl, or benzyl will be mentioned; $R^5$ can be a methylene, ethylene, propylene, or phenylene group. The ammonium and/or phosphonium cation is selected preferably from the group that is formed by N-butylpyrridinium, N-ethylpyridinium, butyl-3 methyl-1 imidazolium, diethylpyrazolium, ethyl-3 methyl-1 imidazolium, pyridinium, trimethylphenylammonium, and tetrabutylphosphonium. As examples of salts that can be used according to the invention, it is possible to cite N-butylpyridinium hexafluorophosphate, N-ethyl pyridinium tetrafluoroborate, tetrabutylphosphonium tetrafluoroborate, butyl-3 methyl-1 imidazolium hexafluoroantimonate, butyl-3 methyl-1 imidazolium hexafluorophosphate, butyl-3 methyl-1 imidazolium trifluoromethylsulfonate, pyridinium fluorosulfonate, and trimethylphenylammonium hexafluorophosphate. These salts can be used alone or in a mixture. They have a solvent function. For example, butyl-3 methyl-1-imidazolium dichlorocuprate, pyridinium tetrachloroborate, butyl-3 methyl-1 imidazolium tetrachloroaluminate, and butyl-3 methyl-1 imidazolium trichlorozincate can also be used.

The dienes and heterodienes and the dienophiles and heterodienophiles that can undergo reaction in a process according to the invention are the compounds which are described in a standard way and examples of which can be found in the book of W. Carruthers Cycloaddition Reactions in Organic Synthesis, Pergamon, Oxford, 1990. Diene and dienophile can be part of the same molecule; intramolecular condensation is then involved.

As examples of dienes, it is possible to cite cyclopentadiene, butadiene, 1,3-cyclohexadiene, methoxybutadiene, dimethylbutadiene, anthracene, 9-hydroxymethylanthracene, furan, with the imine that results from condensation of benzaldehyde with aniline.

As an example of dienophiles, it is possible to cite butadiene, ethylene, 2-butene, methylvinylketone, methylacrylate, ethylacrylate, benzoquinone, naphthoquinone, maleimide, methacrolein, propyne, with the imine that results from the condensation of benzaldehyde with aniline.

Synthesis can be carried out in the presence of at least one catalyst that is then present in the ionic liquid. This catalyst is generally a Lewis acid, such as, for example, the compounds Yb $(OCF_3 CO_2)_3$, Cu $(NO_3)_2$, $CoX_2$, $NiX_2$, $ZnX_2$, $CUX_2$, in which X is the chlorine, the group $OCF_3 SO_3$ or the group $OCF_3 CO_2$ or a transition metal complex.

The compounds that are able to catalyze dienoic condensation and that can be used in the process are those that have been described previously and that are soluble in the ionic media. As an example, $[Cp^*_2Ti(H_2O)_2](CF_3 SO_3)_2$, $[Cp^*Rh$ (diphosphine) $(H_2O)][BF_4]_2$, with $Cp^*$ designating the pentamethylcyclopentadienyl, can be cited.

In the process, it is possible to add an organic solvent that is miscible or partially miscible, such as an aromatic hydrocarbon, and/or a nonmiscible aliphatic hydrocarbon that allows better separation of phases. Preferably, the process is carried out without water.

The quantitative proportion between the reagents and the liquid salt can be between 0.1 and 1000, preferably between 1 and 100. It will be selected so as to obtain the best selectivities.

The molar ratio between the dienophile and the diene can range from 0.1 to 100, preferably from 0.5 to 10.

If a catalyst is used, the concentration of this catalyst in the ionic liquid is not critical. It is advantageously between 1 mmol of compound per liter of salt and 500 mmol per liter, preferably between 2 and 200 mmol per liter, and also between 2 and 100, and even 2 to 50.

The temperature at which condensation will take place will be between −50° C. and 200° C.; advantageously the temperature is less than 100° C., preferably between −20° C. and less than 50° C. The reaction can take place with or without a vapor phase, and the pressure is the autogenous pressure; it can also be increased up to 100 MPa.

The reaction period, which depends on temperature, will be between 1 minute and 10 hours. It will be adjusted to strike a good compromise between conversion and selectivity.

The reaction can be carried out in a closed system, in a half-open system, or continuously with one or more reaction stages. At the outlet of the reactor, the organic phase that contains the reaction products is advantageously separated by simple decanting of the polar phase that contains the salt and can optionally contain a catalyst. The polar phase is, at least in part, returned to the reactor, with the other portion being retreated.

The following examples illustrate the invention without limiting its scope:

EXAMPLE 1

An equimolar mixture of 2.7 g of cyclopentadiene, 2.8 g of methylvinylketone, and 3 ml of butyl-3 methyl-1 imidazolium tetrafluoroborate is introduced into a glass reactor that is equipped with a bar magnet. The two-phase mixture is stirred at room temperature for 25 minutes. During the reaction, samples (0.5 ml) of the reaction mixture, to which heptane is added to improve the separation of products that are formed by the ionic phase, are taken. The cycloaddition (endo/exo) products are analyzed by gas-phase chromatography. The conversion is expressed in moles of cyclopentadiene that are reacted relative to the number of initial moles. The results are summarized in Table 1.

EXAMPLE 2

The operation was carried out as described in Example 1 but using butyl-3 methyl-1 imidazolium hexafluoroantimonate instead of butyl-3 methyl-1 imidazolium tetrafluoroborate.

EXAMPLE 3

The operation was carried out as in Example 1. An equimolar mixture of 2.7 g of cyclopentadiene and 2.8 g of methylvinylketone, 3 ml of butyl-3 methyl-1 imidazolium tetrafluoroborate, and 3 ml of heptane is introduced into the reactor.

EXAMPLE 4
(COMPARISON)

The operation was carried out as in Example 1. A mixture of 2.7 g of cyclopentadiene, 2.8 g of methylvinylketone, and 3 ml of methanol was introduced into the reactor. The reaction mixture is homogeneous.

EXAMPLE 5
(Reaction catalyzed by a Lewis acid)

The operation was carried out as in Example 1. An equimolar mixture of 2.7 g of cyclopentadiene, 2.8 g of methylvinylketone, and 3 ml of butyl-3 methyl-1 imidazolium tetrafluoroborate that contains 0.01M of $Cu^{2+}$ (Cu $(NO_3)_2)$ was introduced into the reactor. An effect of the Lewis acid, which is reflected by an increase in the speed of the reaction, is added to the effect of solvent.

TABLE 1

| Example | Solvent | Reaction period (min) | Conversion (%) | Composition of products (endo/exo) |
|---|---|---|---|---|
| 1 | MBI BF$_4$ | 2 | 84 | 7.4 |
|   |   | 120 | 95 | 6.8 |
|   |   | 480 | 98 | 6.7 |
|   |   | 1440 | 99.8 | 7 |
| 2 | MBI SbF$_6$ | 2 | 49 | 5.9 |
|   |   | 120 | 90 | 5.7 |
|   |   | 480 | 91 | 4.8 |
|   |   | 1440 | 92 | 4.8 |
| 3 | MBI BF$_4$ + heptane | 2 | 25 | 7.5 |
|   |   | 120 | 85 | 4.7 |
|   |   | 480 | 90 | 4.3 |
|   |   | 1440 | 95 | 4.3 |
| 4 | methanol | 2 | 7 | 3.7 |
|   |   | 120 | 75 | 10.2 |
|   |   | 480 | 78 | 10.3 |
|   |   | 1440 | 80 | 10.1 |
| 5 | MBI BF$_4$ + Cu$^{2+}$ | 2 | 90 | 7 |
|   |   | 120 | 96 | 6.5 |
|   |   | 480 | 96 | 6.8 |
|   |   | 1440 | 99.8 | 7.2 |

We claim:

1. A process comprising conducting a dienoic Diels-Alder synthesis, comprising reacting a diene with a dienophile in a medium comprising at least one liquid salt of the formula $Q^+A^-$, in which $Q^+$ represents quaternary ammonium or phosphonium and $A^-$ represents an anion, and at least one catalyst consisting essentially of a Lewis acid.

2. A process according to claim 1, wherein anion $A^-$ is selected from the group consisting of tetrafluoroborate, hexafluorophosphate, hexafluoroantimonate, hexafluoroarsenate, the perfluoroalkylsulfonates, fluorosulfonate or else dichlorocuprate, tetrachloroborate, tetrachloroaluminate, and trichlorozincate.

3. A process according to claim 1, wherein $Q^+$ is selected from the group consisting of the cations of general formula:

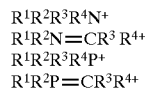

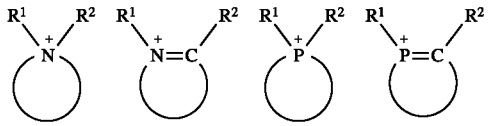

in which R$^1$, R$^2$, R$^3$ and R$^4$, which are identical or different, represent hydrogen, with the exception of NH$_4^+$, or hydrocarbyl radicals that have 1 to 12 carbon atoms, and in which the cycles consist of 4 to 10 atoms.

4. A process according to claim 1, wherein $Q^+$ is of the formula:

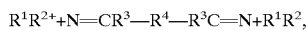

or

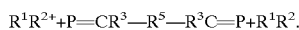

5. A process according to claim 1, wherein the liquid salt selected from the group that consists of N-butylpyrridinium, N-ethylpyridinium, butyl-3 methyl-1 imidazolium, diethylpyrazolium, ethyl-3 methyl-1 imidazolium, pyridinium, trimethylphenylammonium, and tetrabutylphosphonium.

6. A process according to claim 1, wherein the quaternary ammonium or phosphonium salts are selected from the group that consists of N-butylpyridinium hexafluorophosphonate, N-ethyl pyridinium tetrafluoroborate, tetrabutylphosphonium tetrafluoroborate, butyl-3 methyl-1 imidazolium hexafluoroantimonate, butyl-3 methyl-1 imidazolium hexafluorophosphate, butyl-3 methyl-1 imidazolium trifluoromethylsulfonate, pyridinium fluorosulfonate, trimethylphenylammonium hexafluorophosphate, butyl-3 methyl-1 imidazolium dichlorocuprate, pyridinium tetrachloroborate, butyl-3 methyl-1 imidazolium tetrachloroaluminate, and butyl-3 methyl-1 imidazolium trichlorozincate.

7. A process according to claim 1, wherein the diene is cyclopentadiene, butadiene, 1,3-cyclohexadiene, methoxybutadiene, dimethylbutadiene, anthracene, 9-hydroxymethylanthracene, furan, or the imine that results from the condensation of benzaldehyde with aniline.

8. A process according to claim 1, wherein the dienophile is butadiene, ethylene, 2-butene, methylvinylketone, methylacrylate, ethylacrylate, benzoquinone, naphthoquinone, maleimide, methacrolein, propyne, or the imine that results from the condensation of benzaldehyde with aniline.

9. A process according to claim 1, wherein the medium further comprises an organic solvent.

10. A process according to one of the preceding claims, wherein an organic solvent is also used.

11. A process according to claim 1, resulting in an organic phase containing reaction products and said phase is separated from a polar phase containing salt and optionally a catalyst, and said polar phase is at least partly recycled to a reactor wherein the Diels Alder reaction is conducted.

12. A process according to claim 1 operating between −50° and 200° C., under a total pressure up to 100 MPa.

13. Process according to one of claims 1 to 12 operating between −50° and 200° C., under a total pressure that can reach 100 MPa.

14. A process according to claim 1, wherein said Lewis acid is Yb(OCF$_3$ CO$_2$)$_3$, Cu(NO$_3$)$_2$, CoX$_2$, NiX$_2$, ZnX$_2$, CuX$_2$, in which X is chlorine, OCF$_3$ SO$_3$ or OCF$_3$ CO$_2$ or a transition metal complex.

15. A process comprising conducting a dienoic Diels-Alder synthesis comprising reacting a diene with a dienophile in an catalyst-free medium, said medium comprising at least one liquid salt of the formula $Q^+A^-$, in which $Q^+$ represents quaternary ammonium or phosphonium and $A^-$ represents an anion.

16. A process according to claim 15, wherein anion $A^-$ is selected from the group consisting of tetrafluoroborate, hexafluorophosphate, hexafluoroantimonate, hexafluoroarsenate, the perfluoroalkylsulfonates, fluorosulfonate or else dichlorocuprate, tetrachloroborate, tetrachloroaluminate, and trichlorozincate.

17. A process according to claim 15, wherein the $Q^+$ is selected from the group consisting of cations of general formula:

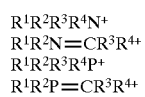

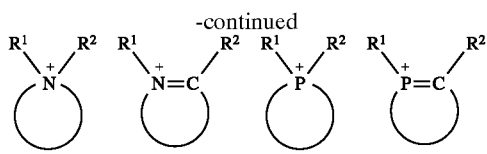

in which $R^1$, $R^2$, $R^3$ and $R^4$, which are identical or different, represent hydrogen, with the exception of $NH^{4+}$, or hydrocarbyl radicals that have 1 to 12 carbon atoms, and in which the cycles consist of 4 to 10 atoms.

18. A process according to claim 15, where $Q^+$ is of the general formula:

$$R^1R^{2+}N\!=\!CR^3\!-\!R^5\!-\!R^3C\!=\!N^+R^1R^2,$$

or $$R^1R^{2+}P\!=\!CR^3\!-\!R^5\!-\!R^3C\!=\!P^+R^1R^2.$$

19. A process according to claim 15, wherein $Q^+$ is selected from the group that consists of N-butylpyridinium, N-ethylpyridinium, butyl-3 methyl-1 imidazolium, diethylpyrazolium, ethyl-3 methyl-1 imidazolium, pyridinium, trimethylphenylammonium, and tetrabutylphosphonium.

20. A process according to claim 15, wherein the liquid salt is selected from the group that consists of N-butylpyridinium hexafluorophosphonate, N-ethyl pyridinium tetrafluoroborate, tetrabutylphosphonium tetrafluoroborate, butyl-3 methyl-1 imidazolium hexafluoroantimonate, butyl-3 methyl-1 imidazolium hexafluorophosphate, butyl-3 methyl-1 imidazolium trifluoromethylsulfonate, pyridinium fluorosulfonate, trimethylphenylammonium hexafluorophosphate, butyl-3 methyl-1 imidazolium dichlorocuprate, pyridinium tetrachloroborate, butyl-3 methyl-1 imidazolium tetrachloroaluminate, and butyl-3 methyl-1 imidazolium trichlorozincate.

21. A process according to claim 15, wherein the diene is cyclopentadiene, butadiene, 1,3-cyclohexadiene, methoxybutadiene, dimethylbutadiene, anthracene, 9-hydroxymethylanthracene, furan, or the imine that results from the condensation of benzaldehyde with aniline.

22. A process according to claim 15, wherein the dienophile is butadiene, ethylene, 2-butene, methylvinylketone, methylacrylate, ethylacrylate, benzoquinone, naphthoquinone, maleimide, methacrolein, propyne, or the imine that results from the condensation of benzaldehyde with aniline.

23. A process according to claim 15, wherein the medium further comprises an organic solvent.

24. A process according to claim 23, wherein the solvent is selected from the group consisting of aromatic hydrocarbons and aliphatic hydrocarbons.

25. A process according to claim 15, resulting in an organic phase containing reaction products and said phase is separated from a polar phase containing salt, and said polar phase is at least partly recycled in a reactor wherein the Diels-Alder reaction is conducted.

26. A process according to claim 15 operating between −50° and 200° C., under a total pressure up to 100 MPa.

* * * * *